United States Patent
Stoertz et al.

(10) Patent No.: US 11,862,034 B1
(45) Date of Patent: Jan. 2, 2024

(54) VARIABLE CONTENT CUSTOMIZATION FOR COACHING SERVICE

(71) Applicant: Verily Life Sciences LLC, Mountain View, CA (US)

(72) Inventors: Aaron Haywood Stoertz, Redwood City, CA (US); Nikhil Roy, Sunnyvale, CA (US); David Wright, Burlingame, CA (US); Peilun Shan, San Francisco, CA (US); Katherine Nadell, San Jose, CA (US); Sarah Abramson, Mountain View, CA (US); Jesse Elds, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 433 days.

(21) Appl. No.: 16/938,612

(22) Filed: Jul. 24, 2020

Related U.S. Application Data

(60) Provisional application No. 62/879,157, filed on Jul. 26, 2019.

(51) Int. Cl.
*G09B 19/00* (2006.01)
*G09B 5/02* (2006.01)
(Continued)

(52) U.S. Cl.
CPC ......... *G09B 19/00* (2013.01); *G06F 16/4387* (2019.01); *G09B 5/02* (2013.01);
(Continued)

(58) Field of Classification Search
CPC ........ G09B 19/00; G16H 20/60; G16H 40/67; H04L 65/60; A61B 5/4842
See application file for complete search history.

(56) References Cited

U.S. PATENT DOCUMENTS

| | | | |
|---|---|---|---|
| 9,288,522 B1 * | 3/2016 | Chang | H04N 21/4532 |
| 2003/0009452 A1 * | 1/2003 | O'Rourke | G06F 16/4387 |

(Continued)

FOREIGN PATENT DOCUMENTS

| | | |
|---|---|---|
| KR | 20140104158 A | 8/2014 |
| KR | 20140104159 A | 8/2014 |

OTHER PUBLICATIONS

V.S. Adamchik, "Linked Lists", Jul. 2011, Carnegie Mellon Univ., pp. 1-8, http://web.archive.org/web/20110710032447/https://www.andrew.cmu.edu/course/15-121/lectures/Linked%20Lists/linked%20lists.html (Year: 2011).*

(Continued)

*Primary Examiner* — Jay Trent Liddle
*Assistant Examiner* — Alyssa N Brandley
(74) *Attorney, Agent, or Firm* — Perkins Coie LLP

(57) ABSTRACT

A computer-implemented method of a coaching service with variable content objects. The method can include invoking a content flow including an ordered sequence of content objects. The content flow is arranged in accordance with a coaching protocol for a user of a user device. The user accesses a coaching service through the user device. The method further includes causing the user device to present a first content object. The first content object is prearranged in the ordered sequence of content objects based on information associated with the user. The method further includes dynamically selecting a second content object to replace a next content object of the ordered sequence of content objects and advancing the content flow to the second content object in lieu of the next content object and in accordance with the coaching protocol.

20 Claims, 7 Drawing Sheets

(51) Int. Cl.

| | |
|---|---|
| *G09B 5/04* | (2006.01) |
| *G09B 5/06* | (2006.01) |
| *G16H 20/60* | (2018.01) |
| *G16H 40/67* | (2018.01) |
| *H04L 65/60* | (2022.01) |
| *A61B 5/00* | (2006.01) |
| *G16H 20/00* | (2018.01) |
| *G06F 16/438* | (2019.01) |
| *H04N 21/466* | (2011.01) |
| *H04N 21/482* | (2011.01) |
| *G16H 50/20* | (2018.01) |
| *G16H 50/70* | (2018.01) |
| *G16H 20/10* | (2018.01) |
| *G16H 20/70* | (2018.01) |

(52) U.S. Cl.
CPC .......... *G09B 5/04* (2013.01); *G09B 5/065* (2013.01); *G09B 19/0092* (2013.01); *G16H 20/00* (2018.01); *G16H 20/60* (2018.01); *G16H 40/67* (2018.01); *H04L 65/60* (2013.01); *H04N 21/4668* (2013.01); *H04N 21/4825* (2013.01); *H04N 21/4826* (2013.01); *A61B 5/4842* (2013.01); *G16H 20/10* (2018.01); *G16H 20/70* (2018.01); *G16H 50/20* (2018.01); *G16H 50/70* (2018.01)

(56) References Cited

U.S. PATENT DOCUMENTS

| | | | | |
|---|---|---|---|---|
| 2006/0218187 | A1* | 9/2006 | Plastina | G06F 16/4387 |
| 2006/0240395 | A1* | 10/2006 | Faist | G09B 7/12 |
| | | | | 434/322 |
| 2007/0156697 | A1* | 7/2007 | Tsarkova | G06F 16/44 |
| | | | | 707/999.009 |
| 2008/0147214 | A1* | 6/2008 | Lee | G06F 16/48 |
| | | | | 707/E17.009 |
| 2008/0242221 | A1* | 10/2008 | Shapiro | H04W 4/029 |
| | | | | 455/3.06 |
| 2008/0319797 | A1* | 12/2008 | Egami | G16H 20/60 |
| | | | | 705/2 |
| 2009/0265356 | A1* | 10/2009 | Hyman | G06Q 30/02 |
| 2010/0017820 | A1* | 1/2010 | Thevathasan | G11B 27/036 |
| | | | | 725/35 |
| 2010/0023544 | A1* | 1/2010 | Shahraray | G11B 27/105 |
| | | | | 707/E17.009 |
| 2010/0179833 | A1* | 7/2010 | Roizen | G06Q 50/2057 |
| | | | | 715/752 |
| 2010/0199295 | A1* | 8/2010 | Katpelly | G06N 5/04 |
| | | | | 725/46 |
| 2011/0314030 | A1* | 12/2011 | Burba | G06F 16/435 |
| | | | | 707/751 |
| 2013/0091054 | A1* | 4/2013 | Nathan | H04N 21/4825 |
| | | | | 715/741 |
| 2014/0023998 | A1* | 1/2014 | Thompson | G09B 5/00 |
| | | | | 434/236 |
| 2014/0024009 | A1* | 1/2014 | Nealon | G09B 5/12 |
| | | | | 434/362 |
| 2014/0156645 | A1 | 6/2014 | Brust et al. | |
| 2014/0335497 | A1* | 11/2014 | Gal | G09B 7/00 |
| | | | | 434/323 |
| 2014/0354434 | A1* | 12/2014 | Lalonde | G06F 16/44 |
| | | | | 340/573.1 |
| 2015/0039644 | A1* | 2/2015 | Trivedi | G06F 16/635 |
| | | | | 707/767 |
| 2015/0074022 | A1* | 3/2015 | Cornelius | G06F 16/95 |
| | | | | 706/12 |
| 2016/0094302 | A1* | 3/2016 | Berner | H04H 60/52 |
| | | | | 700/94 |
| 2016/0293033 | A1* | 10/2016 | Anderson-Hanley | G09B 7/02 |
| 2017/0091408 | A1* | 3/2017 | Bulut | G06F 3/16 |
| 2017/0109479 | A1 | 4/2017 | Vemireddy et al. | |
| 2017/0238039 | A1* | 8/2017 | Sabattini | G06F 16/4387 |
| | | | | 705/14.73 |
| 2017/0277854 | A1* | 9/2017 | Kelly | G16Z 99/00 |
| 2017/0301258 | A1* | 10/2017 | Ram | G09B 5/02 |
| 2018/0096613 | A1* | 4/2018 | Torman | G09B 5/02 |
| 2018/0102064 | A1* | 4/2018 | Thompson | G09B 19/00 |
| 2018/0114591 | A1* | 4/2018 | Pribanic | G06F 40/40 |
| 2018/0121624 | A1* | 5/2018 | Krans | G16H 20/30 |
| 2018/0285410 | A1* | 10/2018 | Attwell | H04H 60/06 |
| 2018/0315499 | A1* | 11/2018 | Appelbaum | G16H 20/70 |
| 2019/0005845 | A1* | 1/2019 | Albert | G09B 5/06 |
| 2019/0013092 | A1* | 1/2019 | Van Halteren | G09B 19/00 |
| 2019/0147760 | A1* | 5/2019 | Bruckner | G10L 25/63 |
| | | | | 706/11 |
| 2019/0159720 | A1* | 5/2019 | Geronimo-Button | A61B 5/4842 |
| 2019/0247718 | A1* | 8/2019 | Blevins | G06F 16/2379 |
| 2020/0129838 | A1* | 4/2020 | Chen | A61B 5/0205 |
| 2020/0267435 | A1* | 8/2020 | Gordon | H04N 21/8586 |
| 2020/0311119 | A1* | 10/2020 | Rönnäng | G06F 3/0482 |

OTHER PUBLICATIONS

Coaching for Activation, http://www.insigniahealth.com/products/cfa; retrieved from the Internet on Jul. 24, 2020; 2 pages, 2020.

Fitbit Health Solutions; https://healthsolutions.fitbit.com/health-coaching/; retrieved from the Internet on Jul. 24, 2020; 4 pages, 2020.

* cited by examiner

VARIABLE CONTENT CUSTOMIZATION FOR COACHING SERVICE

CROSS-REFERENCE TO RELATED APPLICATION

This application claims priority to U.S. provisional patent application Ser. No. 62/879,157 titled "Coaching Service with Variable Next Content Items," filed Jul. 26, 2019, which is incorporated by reference herein in its entirety.

TECHNICAL FIELD

This disclosure generally relates to content customization, and more specifically, to techniques for improving a content flow in a specialized environment, such as for a flow of content objects in a coaching service.

BACKGROUND

Coaching is a form of development in which a coach supports a client in achieving a goal by providing training and/or guidance. Coaching focuses on events of a predetermined sequence to provide the training that incrementally leads the client through objectives to achieve a goal. The sequence of incremental events constitutes a coaching strategy. A coaching strategy is deployed to individuals based on their desired goals. Conforming to a rigid coaching strategy can result in failure to complete the coaching strategy.

For example, in diabetes management, behavioral therapy may be prescribed by a doctor for a coaching recipient to augment the coaching recipient's malfunctioning physiology. A doctor considers numerous factors to formulate a personalized diabetes management program. For example, blood glucose levels, adverse effects of insulin, cost, the likelihood of coaching recipient adherence, and quality of life may be considered when choosing a disease management strategy for a coaching recipient.

The health status of a coaching recipient may change naturally or because of mismanagement due to the tedious and burdensome process required to adhere to a diabetes management program. As such, the coaching recipient risks experiencing diabetes-related complications. A coaching service can help a coaching recipient manage diabetes with ongoing treatment. For example, a coaching service can help a coaching recipient follow a rigid schedule to manage his or her diabetes with ongoing interactions through a smartphone. However, a failure of a coaching service results from an inability by a coach to adapt a coaching strategy to different coaching recipients that have different needs and changing circumstances.

BRIEF DESCRIPTION OF THE DRAWINGS

Various features and parameters of the disclosed technology will become more apparent to those skilled in the art from a study of the Detailed Description in conjunction with the drawings. Embodiments of the disclosed technology are illustrated by way of example and not limitation in the drawings, in which like references indicate similar elements.

Figure 1:
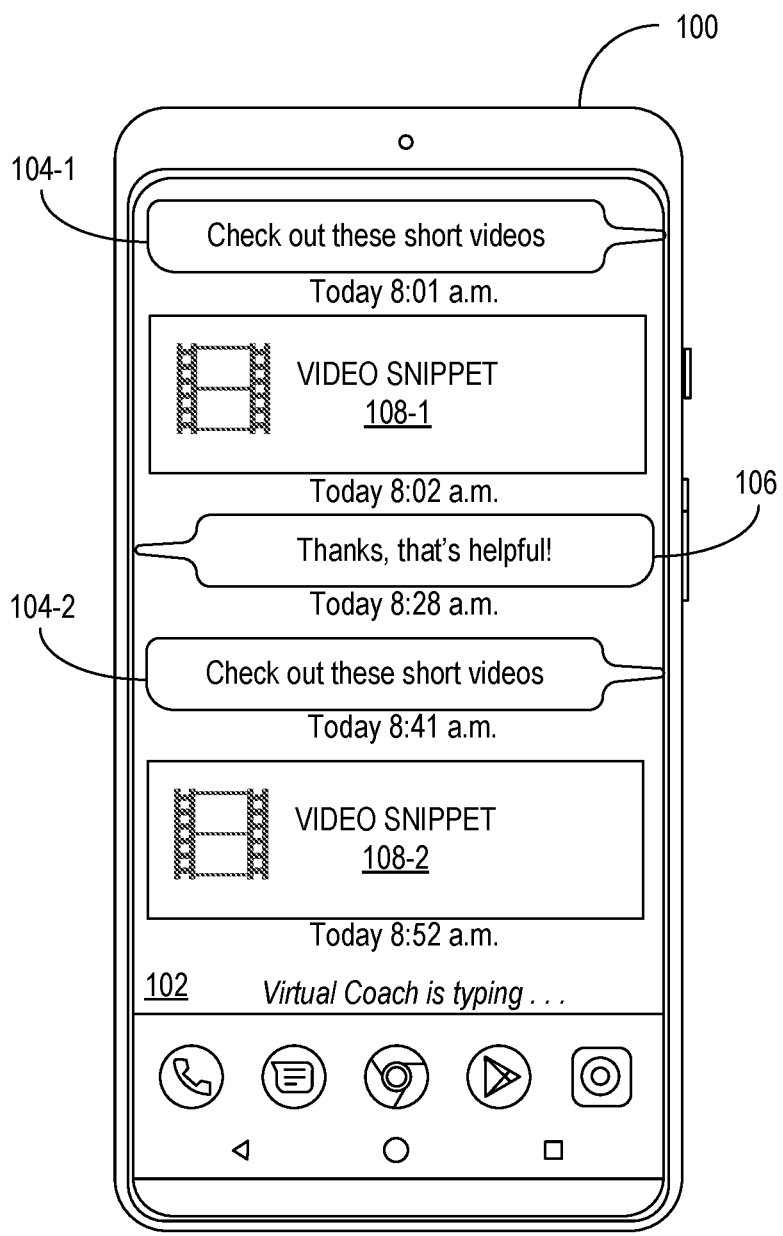
FIG. 1 illustrates a communication exchange on a computing device between a coach and a coaching recipient.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Coaching typically involves a coach that walks a group of individuals through an ordered series of educational content. The coach holds group discussions to reflect on learned content. In an electronic format, the content is provided to users on computing devices. The content can be arranged as a playlist for users of the computing devices. The coach can also engage with individuals in chat rooms to conduct discussions. The educational content cannot be personalized because each individual has specific considerations that are not applicable to the entire group. Likewise, in health-related coaching, educational content is not personalized for coaching recipients (e.g., patients). In some instances, coaching is episodic such that it only occurs when the coaching recipient interacts with a coach due to a medical event. Accordingly, a coaching service for coaching recipients covers content that is not necessarily relevant. As a result, coaching recipients fail to pay attention and, consequently, fail to complete a coaching exercise.

The disclosed solutions overcome the drawbacks of existing techniques. A coaching service adapts variable content objects in a content flow for individual needs. For example, coaching to treat chronic diseases like diabetes or other conditions may involve educational content related to diet, stress levels, and sleep. In some instances, the variable content objects can include medical recommendations. The content flow for an individual participating in a coaching service is adaptable with a targeted set of content that is formulated based on information obtained from various sources such as electronic medical records, pharmacy data, self-reported information (e.g., surveys), indications of preferred content, and monitored data such as that obtained from a continuous glucose monitor. A personalized content flow includes a series of content objects with messages and/or media that goes well beyond replicating in-person coaching. The content objects can be mapped in different combinations to different coaching recipients.

In some embodiments, the coaching service can dynamically recommend relevant content objects that could be shown to the coach's coaching recipient. The recommended content objects could be identified based on data obtained about the coaching recipient. In some embodiments, the content objects are ranked to facilitate selection by the coaching recipient's coach. As such, the coaching service can improve a coaching recipient's experience by providing the selected content in a playlist that maintains the coaching recipient's attention to complete the coaching exercise. Hence, the disclosed coaching service is more efficient both from the perspective of participants and in terms of reducing the demand on network resources.

In some embodiments, the content objects are selected dynamically in real-time or near real-time to enable active learning that depends on recent data pulled from different sources. For example, a content flow can include a series of screens shown to a user on a computing device in accordance with the underlying logic of the coaching service to achieve a predetermined objective of a coaching challenge.

The content flow is presented to a user and/or coach to improve the coach/user relationship. The coaching service can dynamically swap content flows or individual content objects as a user advances through a content flow. As such, a content flow changes to adapt to an individual's needs as determined based on data obtained from various sources. The coaching service can also sort or rank content to rapidly adapt to changing circumstances of an individual.

A frequency of the decision to dynamically change content can vary depending on the availability of data on which the decision is based. For example, a refresh rate to change content of a coaching session can occur rapidly if based on data obtained from a continuous monitoring device. Moreover, the coaching service can throttle the frequency when publishing new content.

An electronic coaching service includes a technical means such as a platform that administers network portals for users to access content for coaching sessions over a medium such as a computer network. A health-related electronic coaching tool can include a playlist of media that is ordered to guide a diabetic patient to learn proper eating habits in a step-by-step manner. For example, a playlist of audio recordings can include lectures that are arranged to coach a patient on how to manage a disease. A coaching service may include different playlists for different categories of coaching recipients to achieve goals. The content flow of a playlist is prearranged before a user begins a coaching session. The playlist is selected based on factors including the coaching recipient's demographic profile, historical information, input from other users of the coaching service, etc. For example, the first playlist for young adults can include a first sequence of content objects while a second playlist for older adults can include a second sequence of content objects.

As used herein, the prefix "pre" that modifies a term refers to occurring "before" or "in advance of." In the context of a content flow, "preselected" content is selected for the content flow before the content flow is played, "prepositioned" content is positioned in a content flow before the content flow is rendered, and "prearranged" or "preset" content is preselected and prepositioned. In contrast, "dynamic" content is affected by the passage of time. For example, dynamically selected content is selected while a content flow is being played (e.g., in real-time or near real-time). Likewise, dynamically positioned or dynamically arranged content is positioned or arranged, respectively, while the content flow is being rendered.

A health-related coaching service can determine a next recommended action for a coach as a function of a combination of factors including a coaching recipient profile, physiological data (e.g., real-time glucose data), coaching recipient's selections, coach's playlist, historical recommended actions and/or compliance with that, and other coaching recipient response patterns with similar profiles (e.g., demographic, disease profile, lab values, medication list, and clinical data). The next recommended action can be to share a specific content object. In some embodiments, a recommended action is weighted more heavily compared to other actions based on how other coaching recipients responded to the recommended action.

In one example, a coaching service can vary content objects of a playlist for a coaching recipient. For example, the coaching service can build a library of coaching content into itemizable "content cards." The content cards can be organized into decks (also referred to as pillars) that are related to a coaching strategy. When a content card is distributed, the coaching service can monitor the coaching recipient's interaction with that particular content card and select similar content cards in the same deck to maintain the coaching recipient's attention. When a coach chooses to send a content card to the coaching recipient, the coaching service can intervene to prompt the coach with suggested content cards in accordance with a coaching strategy.

As used herein, a "content card" may refer to a content object that includes text, images, audio, video snippets, and/or other media. Each content card is designed to educate a coaching recipient in accordance with the objective of a coaching strategy. Content cards can be practical and targeted at behavioral changes, like what to eat and what not to eat. The content cards can be tagged with different keywords or other characteristics that can be used for identifying content cards.

A conventional educational segment of a coaching program is also burdensome because it is time-consuming. For example, a conventional coaching program may include a sequence of daily hour-long videos that each follow interactions with a coach to discuss the videos. In contrast to conventional educational content of coaching services, content cards divide an educational program into discrete snippets. The snippets spare a coaching recipient from the cognitive burden of longer educational segments. For example, a snippet of a 2-hour educational video segment may only be a few minutes or seconds long.

The use of snippets increases the flexibility and variability of a content flow. For example, a segment for diabetes management may include a 60-minute audio lecture that is burdensome for a coaching recipient to consume. By dividing the 60-minute audio segment into 200 snippets that vary between 30 seconds and 2 minutes, coaching recipients can listen to different combinations of the content cards over an extended period. Further, the disclosed embodiments can pinpoint a content card or combination of content cards that have a greater likelihood of improving the effectiveness of coaching.

To aid in understanding, the disclosed embodiments describe an improved coaching service for diabetes management. However, the disclosed technology can be applied to any coaching service or any service that distributes content objects. A diabetes management program can include a prescription for medications and a coaching service for deploying educational content. For example, a doctor can conduct a survey to assess a patient's lifestyle and administer tests to determine a running average of blood-glucose levels (BGLs). In combination with other factors, a coaching service can formulate a diabetes management program to deploy educational content.

In practice, a coaching service for diabetes management involves varying amounts of educational information. A coaching service may include 12 daily videos that are each 60 minutes long. In conjunction with the coaching service, the coaching recipient may be given treatments updated with the active assistance of a coach. The burdensome nature of this form of coaching increases the risk that coaching recipients will simply quit, thereby increasing the likelihood of non-adherence which is substantially more dangerous than just quitting any education program.

The disclosed coaching service is a computer-implemented technology that can help coaching recipients manage diabetes. For example, a mobile application ("app") for self-managing diabetes may include a coaching algorithm such as a chatbot implemented as a virtual or simulated coach. Virtual coaching involves the use of an automated communication device or service such as a chatbot that can engage a coaching recipient with a simulated conversation via a messaging mechanism of a mobile portal or web-based portal on a routine or regular basis.

In some embodiments, a coaching service can collect physiological and contextual information including coaching recipient activity (e.g., metabolic activity/exercise or taking of medication, eating of particular diet, real-time health/activity state from mobile/wearable sensors, self-reported health/activity state), external factors (e.g., longer daylight, average temperature, season, geographical altitude, pollution level, environmental state from mobile/wearable sensors), or coaching recipient profile information (e.g., age, gender, genotype or phenotype information) to improve a content selection algorithm or adjust determined results.

As used herein, a "coach" may refer to a computer-implemented technique for automating coaching processes via a computing device that encourages a user of the computing device to adhere to a given protocol in order to achieve a goal of that protocol. In one example, a coach is an implementation of a chatbot or any automated or semi-automated communications mechanism or device that can communicate with a coaching recipient via a local or network portal. In another example, a coach is a human that uses a computing device to communicate with individuals of a coaching service.

In some embodiments, a virtual coach could be completely automated to function as a human being. As such, the user of a computing device can engage in a simulated natural conversation with the virtual coach. In some embodiments, a virtual coach operates in accordance with a set of rules that are customized for a particular user, a particular type of user, a group of users, etc. In another example, a virtual coach could be partially automated such that a user could influence the way a virtual coach operates live (e.g., in real-time or near real-time) while engaged with a user.

As used herein, a "user" refers to an individual or entity that interacts with content objects of a coaching service via a computing device. For example, a diabetic patient can manage his or her diabetes with a virtual coaching service by consuming educational content. In another example, the user is a coach that interacts with a coaching recipient over a coaching platform to coach the coaching recipient with content objects.

A coach can use a messaging mechanism to improve engagement with a coaching recipient and to share various forms of content objects. Examples of a messenger mechanism include a chat messenger, SMS text, or other input mechanisms that can be used to increase engagement by sharing educational content. In some embodiments, a coach can engage a user in a conversation on a computing device and identify effective content objects for the coaching recipient.

FIG. 1 illustrates a content flow including a communication exchange between a coaching recipient, using a computing device 100, and the coaching recipient's coach during an active coaching session. The coach sends the coaching recipient content objects while being engaged in an SMS text conversation. As illustrated, the computing device 100 is a smartphone with a messaging portal 102 that includes comments from the coach 104-1 and 104-2 and the coaching recipient 106 engaged in a conversation. Although embodied on a smartphone, the messaging portal 102 can run on any computing device that allows the user to obtain content objects which, in this example, are linked video snippets 108-1 and 108-2. The messaging portal 102 can be included in an app or be part of an operating system (OS) of a smartphone or other computing device. The messaging portal 102 can receive messages from the coach to prompt the coaching recipient to consume content objects. In this example, the coach shares links to video snippets 108-1 and 108-2 to help the patient learn to manage a condition. The sharing of content objects can vary by frequency, type, and the amount needed to achieve the desired outcome.

Figure 2:
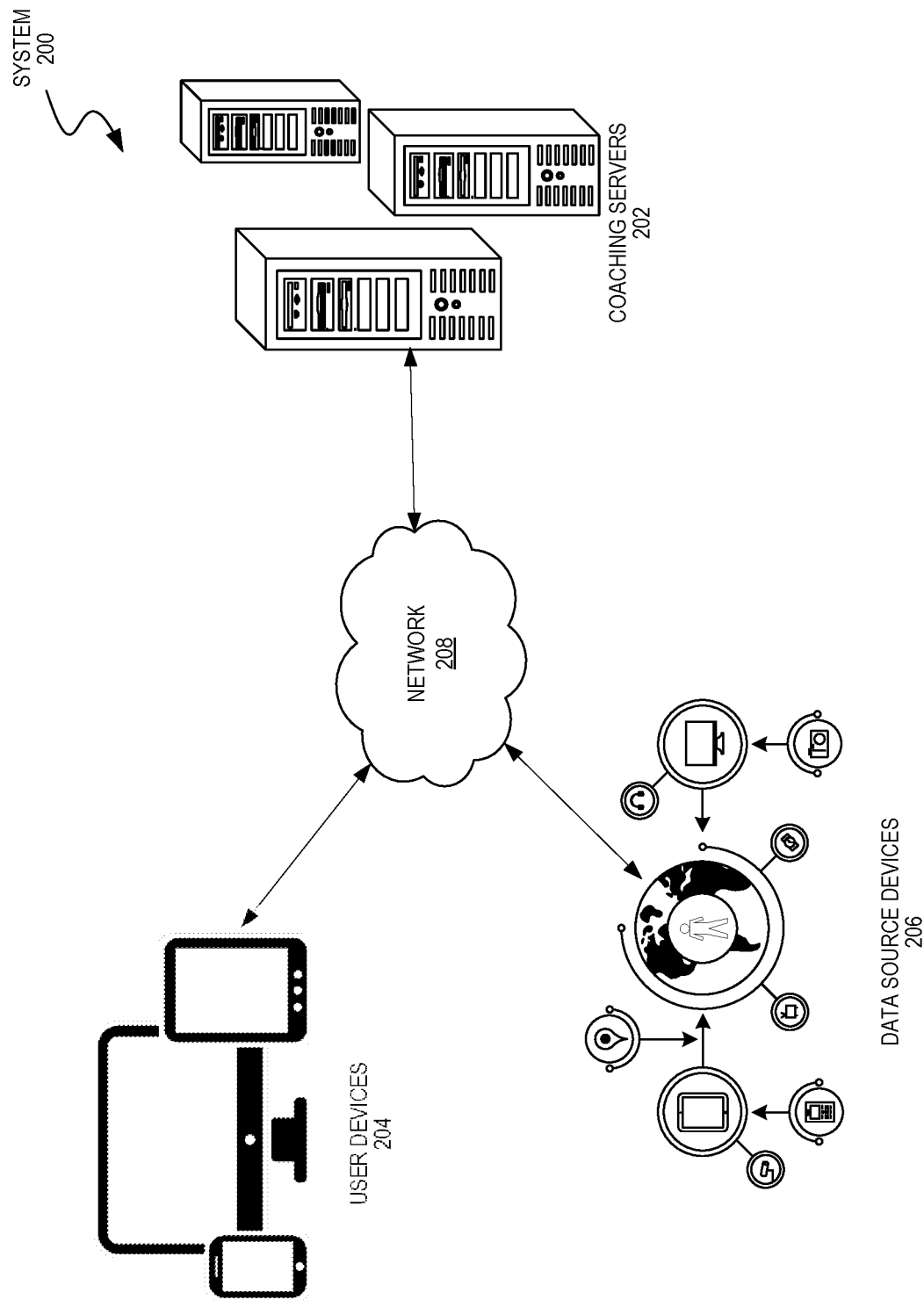
FIG. 2 is a block diagram that illustrates a system that implements a coaching service.

FIG. 2 is a block diagram that illustrates a system 200 that can implement a coaching service. The system 200 can dynamically change a content flow of the coaching service. The system 200 includes components such as coaching servers 202 that run a content engine, user devices 204, and data source devices 206 that collect information used to dynamically change the content flow. The components are all interconnected over a network 208 such as the Internet.

From the perspective of the user devices 204 (also referred to individually as a user device 204), content flows can be embodied as media playlists that can be played on the user devices 204 by advancing through a respective ordered series of content objects to satisfy a coaching protocol (e.g., objective). A particular user device 204 can play a first content object that was preselected from among multiple content objects to play in a position in the series of content objects. Rather than rendering a next content object that was preselected for the series of content objects, a substitute content object is played. The substitute content object can be selected responsive to information collected dynamically from different sources and selected to satisfy a coaching protocol.

From the perspective of the coaching servers 202, the coaching service is administered to facilitate coaching through the user devices 204 by one or more coaches. Each user can access the coaching service over respective user devices 204. The coaching servers 202 can cause each user device 204 to play a first portion of the prearranged content in accordance with a respective coaching protocol for each coaching recipient. The coaching service can then dynamically select a respective second portion of content for each coaching recipient. Each respective second portion of content is configured to substitute a next portion of the prearranged content. The coaching servers 202 can then cause each of the user devices 204 to play a respective second portion of content for each coaching recipient in accordance with the coaching protocol for that coaching recipient.

The network 208 may include any combination of private, public, wired, or wireless portions. The data or information communicated over the network 208 may be encrypted or unencrypted at various locations or along different portions of the network 208. Each component of the system 200 may include combinations of hardware and/or software to process data or information, perform functions, communicate over the network 208, and the like. For example, any component of the system 200 may include a processor, memory or storage, a network transceiver, a display, OS and application software (e.g., for providing a user interface), and the like. Other components, hardware, and/or software included in the system 200 that would be well known to persons skilled in the art are not shown or discussed herein for the sake of brevity.

The user devices 204 can be used to interact with the system 200. Examples of user devices 204 include smartphones (e.g., APPLE IPHONE, SAMSUNG GALAXY, NOKIA LUMINA), tablet computers (e.g., APPLE IPAD, MICROSOFT SURFACE), computers (e.g., APPLE MACBOOK, LENOVO THINKPAD), and any other device that is capable of exchanging data with the coaching servers 202 over the network 208.

The coaching servers 202 may execute a coaching service on any number of server computers that can operate a content engine. The coaching servers 202 can store algorithms to dynamically change content flows of a coaching segment. For example, an algorithm may include a combination of rules for determining whether a content object of a content flow should change.

The data source devices 206 may include any number of servers or other computing resources that can collect, store, and/or provide data or information related to content objects for the coaching servers 202 for use in determining whether to change a content flow. The data source devices 206 may include any source of healthcare-related information. For example, the data source devices 206 may include any providers such as medical facilities, private offices, or devices administered by healthcare professionals. In some embodiments, the data or information may include at least portions of medical records.

Figure 3:
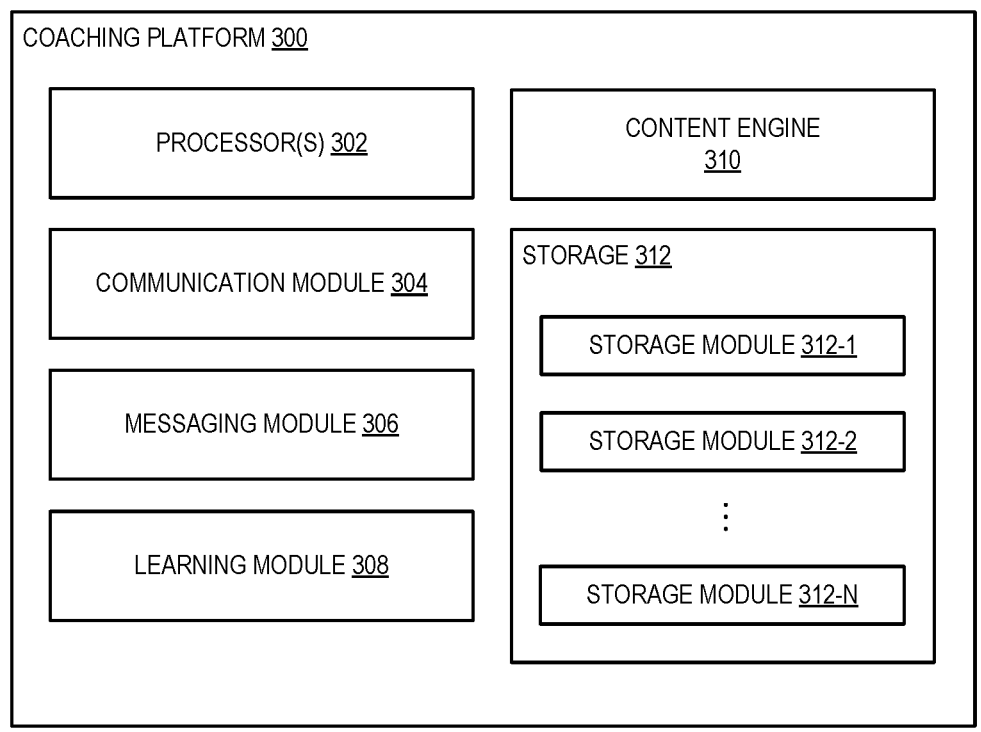
FIG. 3 is a block diagram that illustrates functional components of a coaching service.

FIG. 3 is a block diagram that illustrates functional components of a coaching service. A coaching platform 300 ("platform 300") can include components or modules that collectively operate to perform a process for a coaching service. As used herein, a "component" or "module" may refer to a part or independent unit of hardware and/or software that performs one or more distinct functions. In some instances, a module is self-contained, separable, and/or interchangeable relative to other modules.

As shown, the platform 300 includes one or more processors 302, a communication module 304, a messaging module 306, a learning module 308, a content engine 310, and storage modules 312. Other embodiments of the platform 300 may include some or all of these modules or components, along with other modules and/or components that are within the scope of the disclosure or known to persons skilled in the art but not shown herein for the sake of brevity.

The processor(s) 302 can execute modules from instructions stored in the storage modules 312, which can be any computing device or mechanism capable of storing information. The communication module 304 may manage communications among components of the platform 300 and/or between the platform 300 and another computing device. For example, the communication module 304 can facilitate communication of user inputs or contextual information related to a coaching recipient's coaching experience. The received inputs or information may be wirelessly uploaded by the user's computing device (e.g., the user device 204) or other devices (e.g., data source devices 206) over a network (e.g., network 208) to a server computer (e.g., coaching servers 202).

The communication module 304 facilitates the exchange of communications between a user device and the content engine 310. Further, the communication module 304 may transmit search results to a computing device associated with a coaching recipient or the coaching recipient's coach. The user inputs or contextual information communicated over the communication module 304 can be stored in storage 312, one or more particular storage modules (e.g., storage modules 312-1 through 312-N), a remote storage accessible to the platform 300, or some combination thereof.

The messaging module 306 can generate a messaging interface that allows a user (e.g., a coaching recipient) to interact with content objects of a content flow. The content engine 310 includes underlying logic used to decide when and what content objects to change of a content flow.

In some embodiments, the user input, contextual information, and/or values extracted therefrom can be stored in the storage 312 along with the information used by the content engine 310. In this way, the content engine 310 can improve the recommended content objects for a coaching segment.

In some embodiments, the learning module 308 can utilize the user inputs and/or contextual information to improve the coaching platform 300. For example, the learning module 308 can aggregate collected user inputs and contextual information from numerous users associated with numerous coaching recipients, and process those collected inputs or information in accordance with machine-learning algorithms to train the content engine 310. Examples of machine learning algorithms/techniques include Naïve Bayes Classifier algorithms, K Means Clustering algorithms, Support Vector Machine algorithms, linear regression, logic regression, and artificial neural networks.

The coaching platform 300 can also collect contextual information (e.g., real-time health/activity state from mobile/wearable sensors, self-reported health/activity state, environmental state from mobile/wearable sensors, etc.) to help or improve the search algorithm. Although not shown or described for the sake of brevity, the coaching platform 300 includes modules that ensure compliance with privacy settings and data security.

Figure 4:
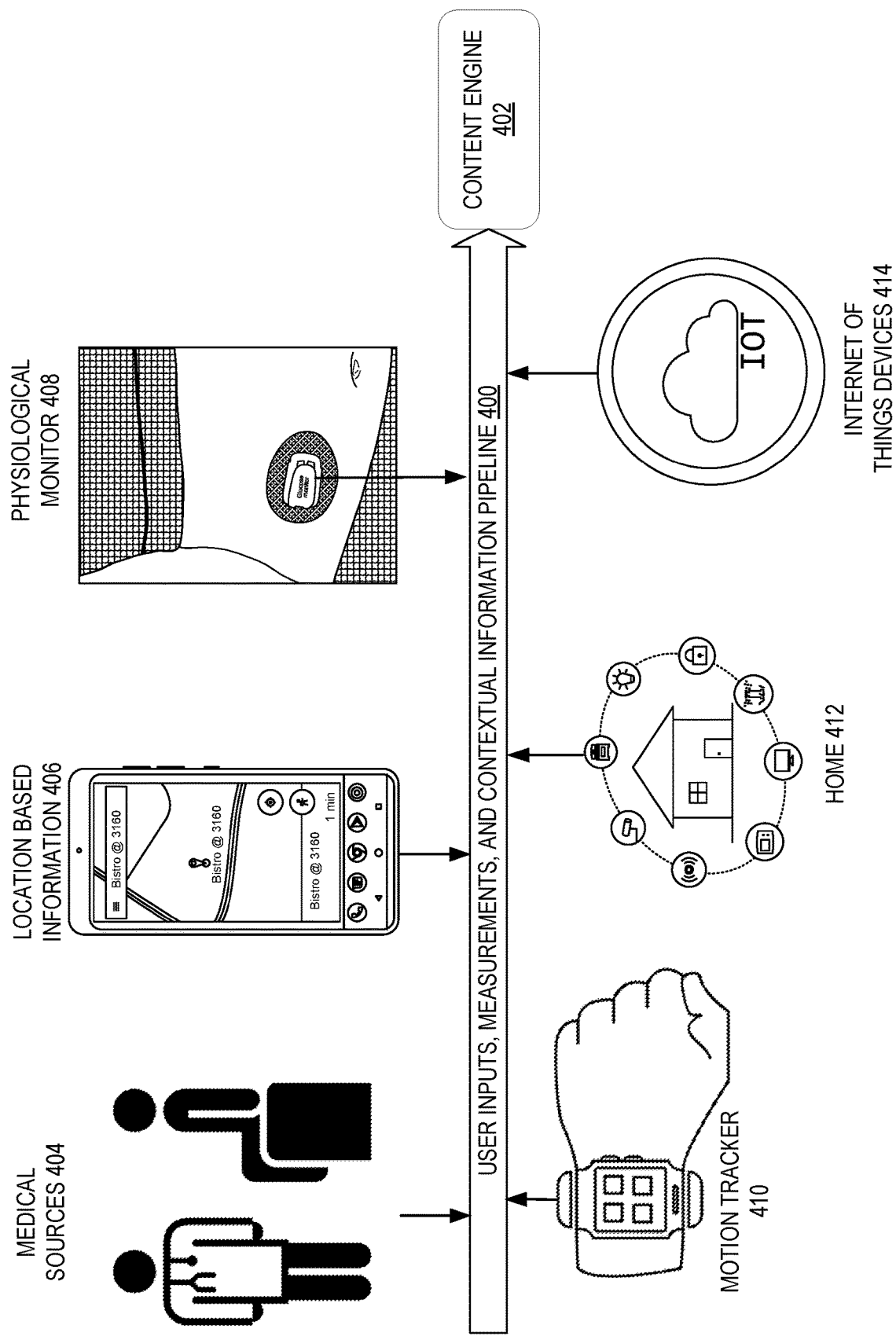
FIG. 4 is a block diagram that illustrates an information pipeline for a content engine.

FIG. 4 is a block diagram that illustrates an information pipeline 400 that communicates data from various sources to a content engine 402, which can formulate content flows and can dynamically change the content flow based on the collected data. The pipeline 400 obtains data and information from various diverse sources for the dynamic engine. The pipeline 400 represents one or more communication channels (e.g., network 208) and devices (e.g., user devices 204 or data source devices 206).

Examples of the diverse sources (e.g., data source devices 206) illustrated in FIG. 4 include medical sources 404, a coaching recipient's location information 406, a physiological monitor 408, a motion tracker 410, monitoring devices at the coaching recipient's home 412, and virtually any other computing devices such as internet of things (IoT) devices 414 that can communicate useful information for the content engine 402.

For example, medical sources 404 can include electronic medical records (EMRs) that describe a coaching recipient's medical history and prescriptions. Examples of the medical sources 404 include hospitals, clinics, pharmacies, or the coaching recipients or medical providers themselves. For example, a coaching recipient can input medical information into an application on a mobile phone when engaged in a discussion with a coach about diabetes management. In addition to the user inputs provided by the user of a computing device, contextual information can be derived from conversations during a coaching session. The medical information can include utilization data that indicates how often a coaching recipient sought medical assistance or experienced an emergency. Other examples of the medical sources 404 include coaching recipient-reported data of surveys or response patterns from other similarly situated coaching recipients.

Examples of location information 406 include a coaching recipient's location, which could be determined by the GPS receiver of the coaching recipient's smartphone. The location information 406 can be used to determine, for example, whether the coaching recipient visited a restaurant or a gym. If so, a coach can engage the coaching recipient to obtain more details about what the user ate at the restaurant or the exercise that the coaching recipient participated in while at the gym. This contextual information can be used by the content engine 402 to determine whether a change in a content flow is required and the degree of the change necessary to manage diabetes.

An example of the physiological monitor 408 is a continuous glucose monitor (CGM) that can continuously collect BGLs of a coaching recipient. The physiological monitor 408 can be worn by the coaching recipient to monitor a physiological parameter of the coaching recipient on a regular basis, continuously throughout the day. Any physiological monitoring device that collects physiological parameter values that are indicative of a condition or useful for managing a condition could be used by the content engine 402 to determine whether a change in a content flow is required and to determine the degree of the required change.

Examples of contextual information from the motion tracker 410 could include data or information about the user's activities such as whether the user is exercising, the duration and rigor of the exercise, and related physiological indicators of the user such as heart rate. This fitness information can be used alone or in combination with other contextual information to influence the outcome of the content engine 402.

Examples of contextual information obtained by monitoring the coaching recipient's home 412 can include intelligent appliances that monitor the user's activities. For example, a smart refrigerator can detect the frequency that a coaching recipient opens the refrigerator and alert the content engine 402 to change a content flow in response to this activity. In another example, the home 412 can include a virtual assistant such as the AMAZON ECHO, which uses natural language processing to match user text and voice inputs to execute commands.

Examples of the IoT devices 414 include any computing devices with sensors that can capture contextual information (e.g., environmental sensors) and that can connect over a network to the content engine 402. The examples shown in FIG. 4 are not meant to be limiting. Rather, the content engine 402 can process user inputs or contextual information from any device capable of generating or capturing the inputs or contextual information and communicating it to the content engine 402.

In some embodiments, user inputs or contextual information can be collected by the pipeline 400 continuously (e.g., periodically, hourly, daily) or on demand. For example, a virtual coaching service can administer a messaging portal that engages a coaching recipient in simulated conversations periodically to receive inputs. The user inputs or contextual information may indicate an ongoing severity of symptoms experienced by the coaching recipient. In some embodiments, these user inputs and contextual information can be used to update the coaching recipient's profile.

In some embodiments, the user inputs or contextual information can be used for compliance monitoring. For example, a mobile app may prompt the user to input whether the coaching recipient is complying with a desired behavior, such as regularly exercising. Tracking a coaching recipient's compliance in combination with data about the coaching recipient's outcomes can be used to determine whether a content flow for diabetes management is effective at managing the coaching recipient's diabetes.

Figure 5:
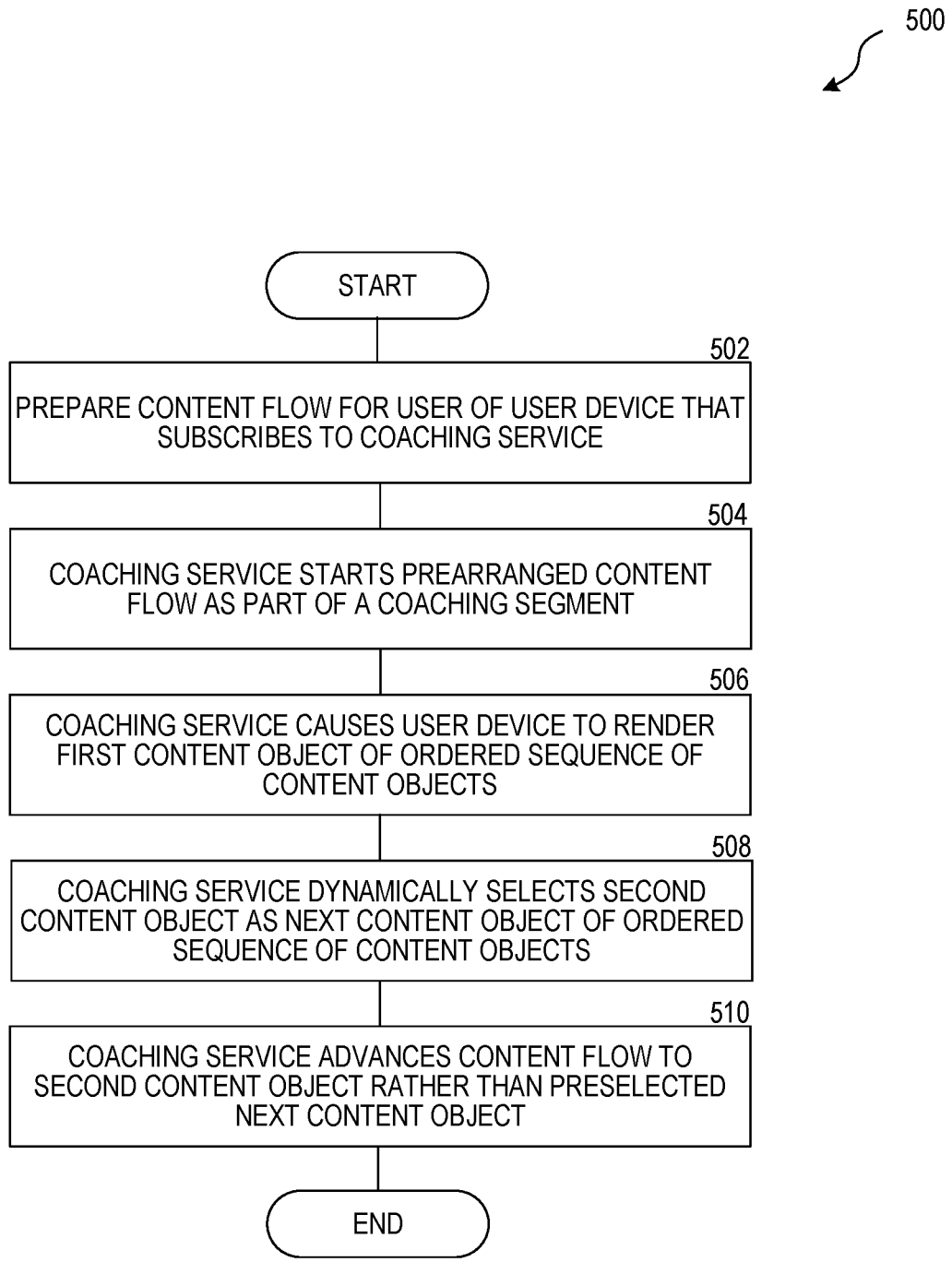
FIG. 5 is a flow diagram that illustrates a method for varying a next content object of a content flow.

FIG. 5 is a flow diagram that illustrates a method for varying a next content object of a content flow according to some embodiments of the present disclosure. In step 502, a coaching service prepares a content flow for a user of a computing device that subscribes to the coaching service. The content flow includes multiple content objects such as video snippets that are ordered in a sequence to provide a coaching experience for the user. In another embodiment, the coaching service can select the content flow from among multiple content flows that are available for users. Each of the content flows can have a different arrangement of different content objects. The content flows can have the same coaching protocol but are customized for different types of users.

In step 504, a coaching service can invoke (e.g., start, continue) a content flow as part of a coaching segment. The content flow includes an ordered sequence of content objects (e.g., media objects, media snippets). The content flow is arranged in accordance with a coaching protocol for coaching a user of a computing device. For example, the user can be a coaching recipient of a health-related coaching service that the coaching recipient accesses on a mobile phone. The coaching protocol of a coaching recipient can include weight management as part of a diabetes management coaching service.

In step 506, the coaching service can cause the computing device to render a first content object of the ordered sequence of content objects. The first content object is preselected and prepositioned in the ordered sequence of content objects before being caused to render on the computing device. The content flow in its entirety can be preset for a user as part of a coaching segment. For example, the content flow can include a series of video snippets to coach a coaching recipient on eating habits as part of a diabetes management segment. Hence, the content flow is based on information associated with the user such as the user being diabetic.

In step 508, the coaching service dynamically selects and presents a second content object to replace a next content object of the ordered sequence of content objects. Like the first content object, the next content object was preselected and prepositioned in the ordered sequence of content objects based on information associated with the user. The second content object is different from the next content object. In some embodiments, the second content object is selected in response to an indication to continue the content flow.

In one example, the user is a patient, the coaching protocol is for managing a condition of the patient, and the second content object is dynamically selected based on a monitored physiological parameter of the patient such as BGLs obtained from a CGM worn by the coaching recipient. For example, the first content object may be a video snippet including an introduction to diabetes management. The next content object could be a video snippet about engaging in exercise for control weight. However, given data that a coaching recipient has recently frequented fast food restaurants via a location tracking application on the coaching recipient's mobile phone, the next content object may be swapped for a different video snippet about making suitable food choices to control weight.

Figure 6:
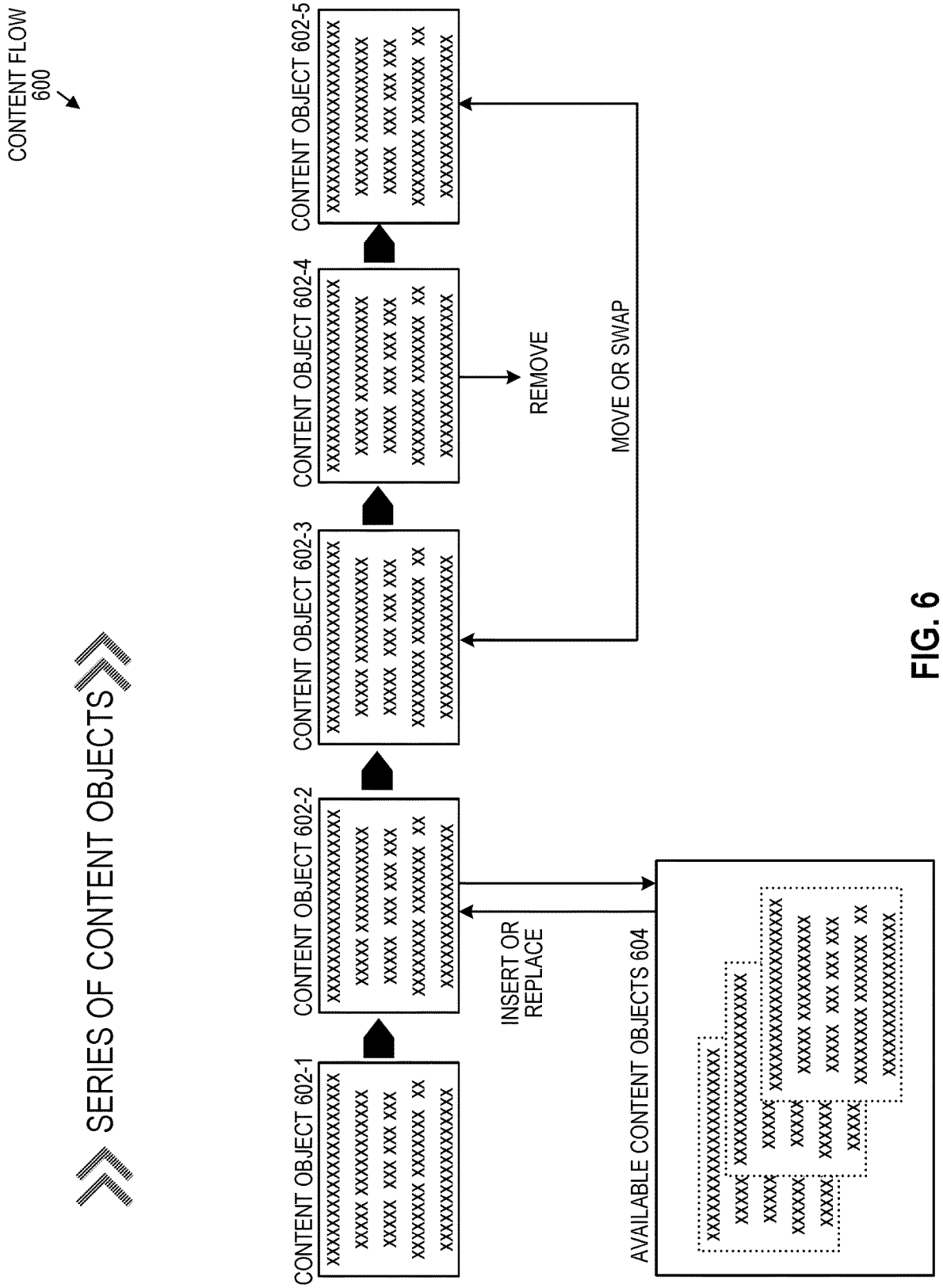
FIG. 6 is a block diagram that illustrates dynamic modifications of a content flow with variable next content objects.

The content flow can vary in different ways to satisfy a coaching protocol. For example, FIG. 6 is a block diagram that illustrates a dynamic modification of a content flow with variable next content objects. The content flow 600 is functionally equivalent to an index of ordered elements that are rendered to illustrate a coaching segment. In the illustrated embodiment, the elements of the content flow 600 are content objects that are played on a computing device.

The content flow 600 includes an ordered series of content objects 602-1 through 602-5. Each content object and its respective position in the order of content objects relative to each other are preselected based on information about the user such as a medical condition, prescription, activity, and/or demographic information. The coaching service can create the content flow 600 for the user or an existing content flow can be selected for a user. In one example, the content object 602-2 is dynamically inserted between the content object 602-1 and 602-3 to become a next content object after the content object 602-1 in the series of content objects of the content flow 600. In this case, the number of content objects of a content flow 600 increases by one to include the content object 602-2.

In another example, the content object 602-2 is the next content object and is replaced with a different content object from the available content objects 604. As such, the number of content objects of a content flow 600 does not change. In another example, the content object 602-4 is a next content object that is removed from the content flow 600. As such, the number of content objects of the content flow 600 decreases by one due to the removed next content object 602-4. In another example, the content object 602-3 is moved in the ordered series of content objects after content object 602-4. In yet another illustrated example, the content objects 602-3 and 602-5 are swapped such that the number of content objects of the content flow 600 does not change despite the order of the content flow changing.

In some embodiments, a substitute content object is selected by a coach of the user. For example, the coaching service can dynamically select a variety of alternative content objects and present those alternatives as recommendations for the coach to select during a coaching exercise. The coaching service then receives an indication that the coach selected the substitute content object for the coaching recipient.

Referring back to FIG. 5, in step 510, the coaching service advances the content flow to the second content object in lieu of the next content object and in accordance with the coaching protocol. The dynamic selection of the content object not only aids to provide relevant and timely content but can also help avoid premature termination of the content flow by the user of the computing device. For example, if the user repeatedly restarts playback of a content object but fails to complete it, the coaching service can replace that content object with another content object that facilitates satisfying the coaching protocol.

A content flow is not limited to a playlist of a series of content objects on a computing device. Instead, an interface that facilitates a coaching process can be utilized. A content flow can be text-based or be voice-based where audio content is played over an audio channel. In some embodiments, a content flow can include a combination of different forms of content objects that can be played on one or more computing devices.

Figure 7:
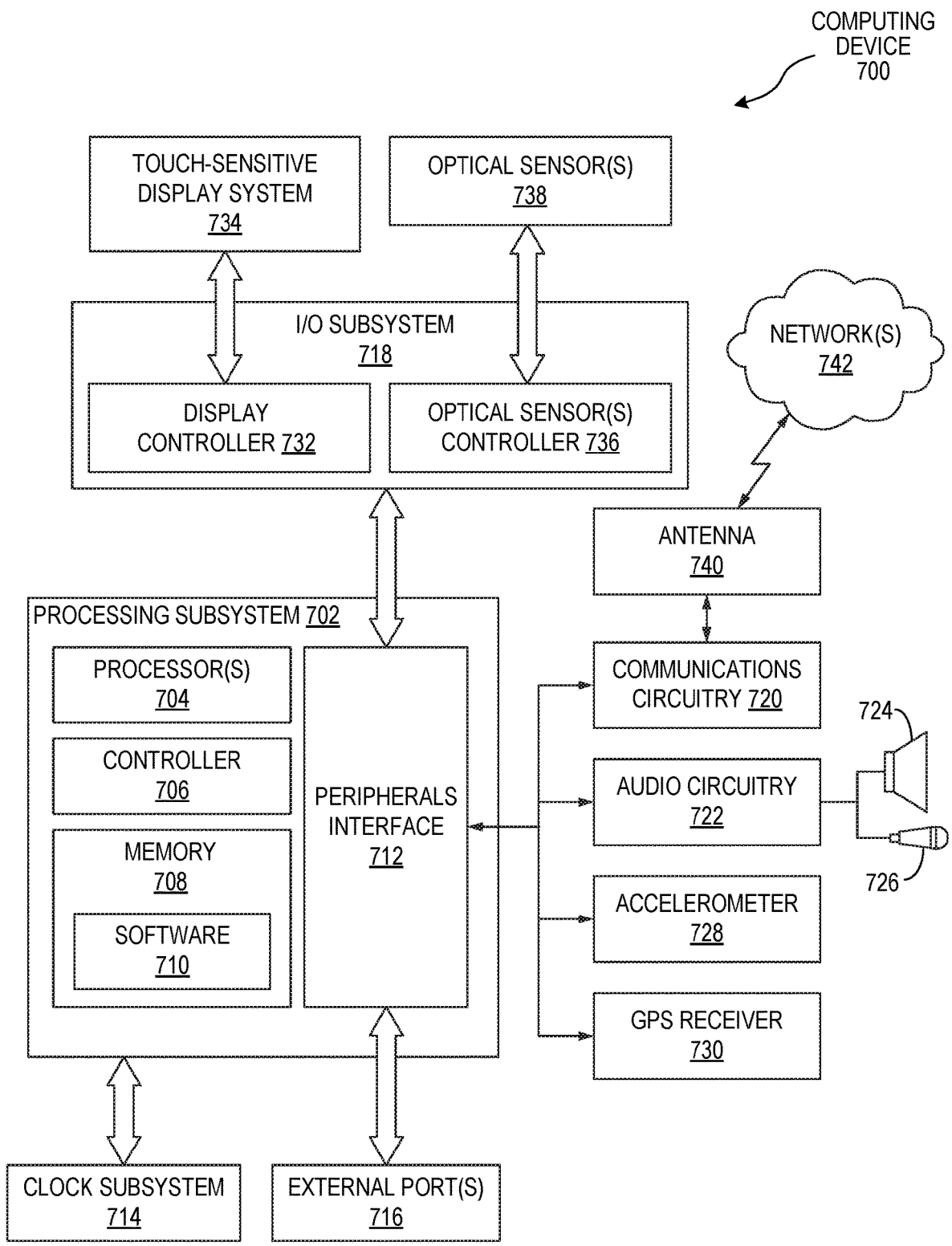
FIG. 7 is a block diagram that illustrates an example computing device in which aspects of the disclosed technology can be embodied.

FIG. 7 is a block diagram that illustrates an example computing device (e.g., computing device 100) in which aspects of the disclosed technology can be embodied. For example, the coaching platform 300 of FIG. 3 may be hosted on the computing device 700. The computing device 700 may include generic components and/or components specifically designed to carry out the disclosed technology. The computing device 700 may be a standalone device or part of a distributed system (e.g., system 200 of FIG. 2) that spans networks, locations, machines, or combinations thereof. For example, components of the computing device 700 may be included in or coupled to a system-on-chip (SOC), a single-board computer (SBC) system, a desktop or laptop computer, a kiosk, a mainframe, a mesh of computer systems, or combinations thereof.

In some embodiments, the computing device 700 can operate as a server device or a client device in a client-server network environment, or as a peer machine in a peer-to-peer system. In some embodiments, the computing device 700 may perform one or more steps of the disclosed embodiments in real-time, near real-time, offline, by batch processing, or combinations thereof.

The computing device 700 includes a processing subsystem 702 that includes one or more processors 704 (e.g., central processing units (CPUs), application specific integrated circuits (ASICs), and/or field programmable gate arrays (FPGAs)), a memory controller 706, memory 708 that can store software 710, and a peripherals interface 712. The memory 708 may include volatile memory (e.g., random-access memory (RAM)) and/or non-volatile memory (e.g., read-only memory (ROM)). The memory 708 can be local, remote, or distributed. The computing device 700 can also include a clock subsystem 714 that controls a timer for use in some embodiments. The components of the computing device 700 are interconnected over a bus (not shown) operable to transfer data between hardware components.

The peripherals interface 712 is coupled to one or more external ports 716 which can connect to an external power source, for example. The peripherals interface 712 is also coupled to an I/O subsystem 718. Other components coupled to the peripherals interface 712 include communications circuitry 720, audio circuitry 722 for a speaker 724 and a microphone 726, an accelerometer 728, a GPS receiver 730 (or global navigation satellite system (GLONASS) or other global navigation system receiver), and other sensors (not shown). The GPS receiver 730 is operable to receive signals concerning the geographic location of the computing device 700. The accelerometer 728 can be operable to obtain information concerning the orientation (e.g., portrait or landscape) of the computing device 700.

The I/O subsystem 718 includes a display controller 732 operative to control a touch-sensitive display system 734, which further includes the touch-sensitive display of the computing device 700. The I/O subsystem 718 also includes an optical sensor(s) controller 736 for one or more optical sensors 738 of the computing device 700. The I/O subsystem 718 includes other components (not shown) to control physical buttons.

The communications circuitry 720 can configure the antenna 740 of the computing device 700. In some embodiments, the antenna 740 is structurally integrated with the computing device 700 (e.g., embedded in the housing or display screen) or coupled to the computing device 700 through the external ports 716. The communications circuitry 720 can convert electrical signals to/from electromagnetic signals that are communicated by the antenna 740 to networks 742 (e.g., network 208 of FIG. 2) or other devices. For example, the communications circuitry 720 can include radio frequency (RF) circuitry that processes RF signals communicated by the antenna 740.

The communications circuitry 720 can include circuitry for performing well-known functions such as an RF transceiver, one or more amplifiers, a tuner, oscillators, a digital signal processor, a CODEC chipset, a subscriber identity module (SIM card or eSIM), and so forth. The communications circuitry 720 may communicate wirelessly via the antenna 740 with the networks 742 (e.g., the Internet, an intranet and/or a wireless network, such as a cellular network, a wireless local area network (LAN) and/or a metropolitan area network (MAN)) or other devices.

The software 710 can include an OS software program, application software programs, and/or modules (e.g., the communication module 304, messaging module 306, learning module 308, content engine 310, storage modules 312 of FIG. 3). For example, a GPS module can determine the location of the computing device 700 based on the GPS signals received by the GPS receiver 730. The GPS module can provide this information to components of the computing device 700 for use in various applications (e.g., to provide location-based contextual information).

A software program, when referred to as "implemented in a computer-readable storage medium," includes computer-readable instructions stored in the memory (e.g., memory 708). A processor (e.g., processors 704) is "configured to execute a software program" when at least one value associated with the software program is stored in a register that is readable by the processor. In some embodiments, routines executed to implement the disclosed embodiments may be implemented as part of OS software (e.g., MICROSOFT WINDOWS® and LINUX®) or a specific software application, component, program, object, module, or sequence of instructions referred to as "computer programs."

Computer programs typically comprise one or more instructions set at various times in various memory devices of the computing device 700, which, when read and executed by the processor 704, will cause the computing device 700 to execute functions involving the disclosed embodiments. In some embodiments, a carrier containing the aforementioned computer program product is provided. The carrier is one of an electronic signal, an optical signal, a radio signal, or a non-transitory computer-readable storage medium (e.g., the memory 708).

Operation of the memory 708, such as a change in state from a binary one (1) to a binary zero (0) (or vice versa) may comprise a visually perceptible physical change or transformation. The transformation may comprise a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

The computing device 700 may include other components that are not shown nor further discussed herein for the sake of brevity. One having ordinary skill in the art will understand any hardware and software that is included but not shown in FIG. 7. While embodiments have been described in the context of fully functioning computing devices, those skilled in the art will appreciate that the various embodiments are capable of being distributed as a program product in a variety of forms and that the disclosure applies equally, regardless of the particular type of machine or computer-readable media used to actually effect the embodiments.

Remarks

The embodiments set forth above represent necessary information to enable those skilled in the art to practice the embodiments and illustrate the best mode of practicing the embodiments. Upon reading the following description in light of the accompanying Figures, those skilled in the art will understand the concepts of the disclosure and will recognize applications of these concepts that are not particularly addressed herein. It should be understood that these concepts and applications fall within the scope of the disclosure and the accompanying claims.

The purpose of the terminology used herein is only for describing embodiments and is not intended to limit the scope of the disclosure.

Reference to "one embodiment" or "an embodiment" means that a particular feature, structure, or parameter described in connection with the embodiment is included in at least one embodiment of the disclosure. The appearances of the phrase "in one embodiment" in this disclosure are not necessarily referring to the same embodiment, nor are separate or alternative embodiments necessarily mutually exclusive of other embodiments. Moreover, various features are described that may be exhibited by some embodiments and not by others. Similarly, various requirements are described that may be requirements for some embodiments and not for other embodiments.

As used herein, unless specifically stated otherwise, terms such as "processing," "computing," "calculating," "determining," "displaying," "generating," or the like, refer to actions or processes of an electronic device that manipulates and transforms data, represented as physical (electronic) quantities within the computer's memory or registers, into other data similarly represented as physical quantities within the device's memory, registers, or other such storage medium, transmission, or display devices.

When used in reference to a list of multiple items, the word "or" is intended to cover all of the following interpretations: any of the items in the list, all of the items in the list, and any combination of items in the list.

Unless the context clearly requires otherwise, throughout the description and the embodiments, the words "comprise," "comprising," and the like are to be construed in an inclusive sense, as opposed to an exclusive or exhaustive sense; that is to say, in the sense of "including, but not limited to."

As used herein, the terms "connected," "coupled," or any variant thereof, means any connection or coupling, either direct or indirect, between two or more elements; the coupling of or connection between the elements can be physical, logical, or a combination thereof. For example, two components may be coupled directly to one another or via one or more intermediary channels or components. As another example, devices may be coupled in such a way that information can be passed therebetween, while not sharing any physical connection with one another. Where context permits, words in the Detailed Description using the singular or plural form may also include the plural or singular form, respectively.

The foregoing description of various embodiments of the described subject matter has been provided for the purposes of illustration and description. It is not intended to be exhaustive or to limit the described subject matter to the precise forms disclosed. Many modifications and variations will be apparent to one skilled in the art. Embodiments were chosen and described in order to best describe the principles of the invention and its practical applications, thereby enabling those skilled in the relevant art to understand the described subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by this disclosure. Particular terminology used when describing certain features or aspects of various embodiments should not be taken to imply that the terminology is being redefined herein to be restricted to any specific parameters, features, or aspects of the technology with which that terminology is associated. In general, the terms used in the following described should not be construed to limit the technology to the specific embodiments disclosed in the specification, unless those terms are explicitly defined herein. Accordingly, the actual scope of the technology encompasses not only the disclosed embodiments but also all equivalent ways of practicing or implementing the embodiments.

The invention claimed is:

1. A computer-implemented method comprising:
    invoking a content flow of a coaching service including an ordered sequence of content objects,
    wherein the sequence of content objects is ordered in accordance with a coaching protocol for coaching a user of a user device;
    causing the user device to present a first content object of the ordered sequence of content objects,
    wherein the first content object is preset in the ordered sequence of content objects based on a condition of the user;
    detecting multiple interruptions to presenting the first content object on the user device,
    wherein the multiple interruptions to presenting the first content object are caused by the user;
    in response to detecting the multiple interruptions, dynamically selecting a second content object, in accordance with the condition of the user, to replace the first content object in lieu of a next content object in the ordered sequence of content objects,
    wherein the next content object is preset in the ordered sequence of content objects based on the condition of the user, and
    wherein the second content object is different from the next content object; and
    advancing the content flow to cause the user device to present the second content object rather than the next content object,
    wherein the second content object is presented on the user device in accordance with the coaching protocol.

2. The method of claim 1, wherein the second content object is selected responsive to an indication to continue the content flow.

3. The method of claim 1, wherein the second content object is inserted between the first content object and the next content object in the ordered sequence of content objects.

4. The method of claim 1, wherein the second content object replaces the next content object in the ordered sequence of content objects.

5. The method of claim 1, wherein the next content object is removed from the ordered sequence of content objects.

6. The method of claim 1, wherein the next content object is moved to a different position in the ordered sequence of content objects.

7. The method of claim 1, wherein the condition is associated with a disease and the coaching protocol is for managing the disease of the user.

8. The method of claim 1, wherein the coaching protocol is for improving the condition of the user.

9. The method of claim 1, wherein the condition includes a diabetic condition and the coaching protocol is for improving the diabetic condition.

10. The method of claim 1, wherein the second content object is selected by a coach of the user.

11. The method of claim 1, wherein dynamically selecting the second content object comprises:
    presenting a set of selectable content objects to a coach of the user, the set of selectable content objects including the second content object; and
    receiving an indication that the coach selected the second content object from among the set of selectable content objects.

12. The method of claim 1, wherein the coaching protocol is for treating a disease of the user, and wherein the second content object is dynamically presented based on a monitored physiological parameter of the user.

13. The method of claim 1, wherein the ordered sequence of content objects is an ordered sequence of media snippets.

14. The method of claim 1 further comprising, prior to invoking the content flow:
    creating the content flow based on the condition of the user,
    wherein the content objects and the ordered sequence are personalized for the user.

15. The method of claim 1 further comprising, prior to invoking the content flow:
    receiving a selection of the content flow from among a plurality of content flows that are available for the user.

16. A computer-implemented method comprising:
    processing a media playlist by advancing through an ordered series of media objects in accordance with a protocol,
    wherein the media playlist is presented on a user device by playing the ordered series of media objects including:
        playing a first media object that is preset in a position of the ordered series of media objects relative to other media objects;
        detecting multiple interruptions to the playing of the first media object on the user device,
        wherein the multiple interruptions to the playing of the first media object are caused by the user; and
        in response to detecting the multiple interruptions, playing a substitute media object instead of playing the first media object, such that the substitute media object is played before a next media object that was preset in the ordered series of media objects,
        wherein the substitute media object is selected responsive to data collected from a plurality of data sources and in accordance with the protocol.

17. The method of claim 16, wherein playing the ordered series of media objects comprises:
    playing the next media object on the user device.

18. The method of claim 16, wherein playing the ordered series of media objects comprises:

reordering the ordered series of media objects while the ordered series of media objects is playing on the user device.

19. A server computer comprising:

one or more memories storing instructions of a coaching service that is configured to facilitate virtual coaching by a coach of a plurality of coaching recipients, wherein each coaching recipient is a user of a user device capable of communicatively coupling to the server computer;

one or more processors configured to execute the instructions stored on the one or more memories, causing each user device to:
- play a first portion of media on each user device in accordance with a respective playlist for each coaching recipient; and
- detect multiple interruptions to playback of the first portion of media on a user device,
  - wherein the multiple interruptions to playback of the first portion of media are caused by the user;
- in response to detecting the multiple interruptions, play a second portion of the media for each coaching recipient in accordance with a coaching protocol for each coaching recipient,
  - wherein each respective second portion of the media is configured to substitute the first portion of the media in lieu of a next portion of the media.

20. The server computer of claim 19, wherein each respective second portion of media is selected by a single coach from among a plurality of portions of the media.

\* \* \* \* \*